United States Patent [19]

Post

[11] Patent Number: Plant 6,564

[45] Date of Patent: Jan. 24, 1989

[54] KALANCHOE PLANT NAMED HELGOLAND

[75] Inventor: Joachim Post, Kirchlinteln, Fed. Rep. of Germany

[73] Assignee: Fides Beheer B.V., De Lier, Netherlands

[21] Appl. No.: 60,673

[22] Filed: Jun. 11, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of Kalanchoe plant named Helgoland, characterized by its light red flower color, strong growth habit, free branching habit, average 11 week flowering response, and its ability to adapt to production in 10–12 cm pots.

1 Drawing Sheet

The present invention relates to a new and distinct cultivar of Kalanchoe plant, botanically known as *Kalanchoe blossfeldiana,* referred to by the cultivar name Helgoland.

Helgoland is a spontaneous mutation of Singapore, and was discovered by applicant in a controlled environment in a bed of flowering plants of the parent Singapore in Kirchlinteln, Federal Republic of Germany in the spring of 1982. Helgoland was discovered due to its significantly different red flower color.

Asexual reproduction of Helgoland by shoot cuttings, as performed by me at Kirchlinteln, Federal Republic of Germany in 1982 has demonstrated that the combination of characteristics as herein disclosed for the new cultivar are firmly fixed and are retained through successive generations of asexual reproduction.

Helgoland has not been observed under all possible environmental conditions. The phenotype may vary significantly with variations in environment such as temperature, light intensity and day length. The following observations, measurements and values describe the new cultivar as grown in De Lier, The Netherlands, under greenhouse conditions which closely approximate those generally used in commercial practice.

The following traits have been repeatedly observed and are determined to be basic characteristics of Helgoland, which in combination distinguish this Kalanchoe as a new and distinct cultivar:

1. Excellent red flower color.
2. Strong growth.
3. Freely branching, with shoots formed at every node.
4. Suitable for production in 10–12 cm pots.
5. Highly floriferous, with numerous flowers formed at every shoot.
6. To reduce peduncle elongation after flower initiation, plants must be treated with Alar/B9 or Bonzi.

The cultivar most similar to Helgoland is the parent cultivar Singapore. Helgoland is principally distinguished from Singapore by its flower color, with Singapore being a more intense, vivid red. Singapore also has more fading, with Helgoland essentially retaining its color.

The accompanying photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values are taken under natural light conditions at approximately 10:00 a.m. in De Lier, The Netherlands.

Botanical classification: *Kalanchoe blossfeldiana,* cv. Helgoland.

Parentage: Spontaneous mutation of Singapore.

Propagation: The new cultivar holds its distinguishing characteristics through successive propagations by leaf cuttings and by division of shoots.

(A) *Type cutting.*—Shoot cutting.

(B) *Time to root.*—Summer: 12 days at 21°; winter, 17 days.

(C) *Rooting habit.*—Large, thick roots.

Plant description:

(A) *Form.*—Upright, medium sized; growing and scheduling practices can produce medium or larger sized plants.

(B) *Habit of growth.*—Good growth rate for this type of plant; shoots are normally formed at every node.

(C) *Foliage description.*—Leaves simple, opposite, generally symmetrical. (1) Size: Average, full grown leaf of a flowering plant of Helgoland when grown in a 10 cm pot is 90 mm long and 65 mm wide. (2) Shape: Ovate, apex obtuse, base truncate. (3) Texture: Glabrous, coriaceous, succulent. (4) Margin: Slightly crenate. (5) Color: Young foliage top side 137A, under side 137B. Mature foliage top side 137A, under side 137B.

Flowering description:

(A) *Flowering habit.*—Inflorescence of each shoot is formed by dichotomous branching, starting with opening of terminal flower at main axis, followed by terminal flowers of the side branches of the inflorescence. Opening of new buds will continue for 9 weeks or more. Individual flowers last 2 weeks or more after opening.

(B) *Natural flowering season.*—November. Flowering time under controlled day length at 25° C. in summer is 10 weeks; in winter at 20° C., 12 weeks. Flowering time depends on temperature, light intensity and other growing conditions.

(C) *Flower buds.*—Oblong, developing to tubular as petals mature, sheathed with four green sepals; corolla at maturity about 9 mm. (1) Size: 10 mm. (2) Shape: Oblong. (3) Rate of opening: Normal.

(D) *Flowers borne.*—Compound dichasial cyme on fairly strong peduncles. Peduncle length depends on growing conditions and B9/Alar applications. Peduncles up to 6 mm long.

(E) *Quantity of flowers.*—Very floriferous with new buds continuing to develop.

(F) *Petals.*—(1) Shape: Nearly round, apex cuspidate. (2) Color: Top side when opening, 46C, with little or no fading; under side, 46D. (3) Number and size of petals: Four (4), united in corolla; petals 6 mm in diameter, total flower diameter 14 mm.

(G) *Reproductive organs.*—(1) Stamens: Eight (8) in number. (a) Anther shape: Flat, elliptical. (b) Filament color: Yellow. (c) Pollen color: Yellow. (2) Pistils: (a) Stigma shape: Flat, crystalline. (b) Style color: Light green-yellow. (c) Ovaries: 4-celled, 7 mm long, light green.

Disease resistance: No known Kalanchoe diseases observed to date.

I claim:

1. A new and distinct cultivar of Kalanchoe plant named Helgoland, as described and illustrated, and particularly characterized by its light red flower color, strong growth habit, free branching habit, average 11 week flowering response, and its ability to adapt to production in 10–12 cm pots.

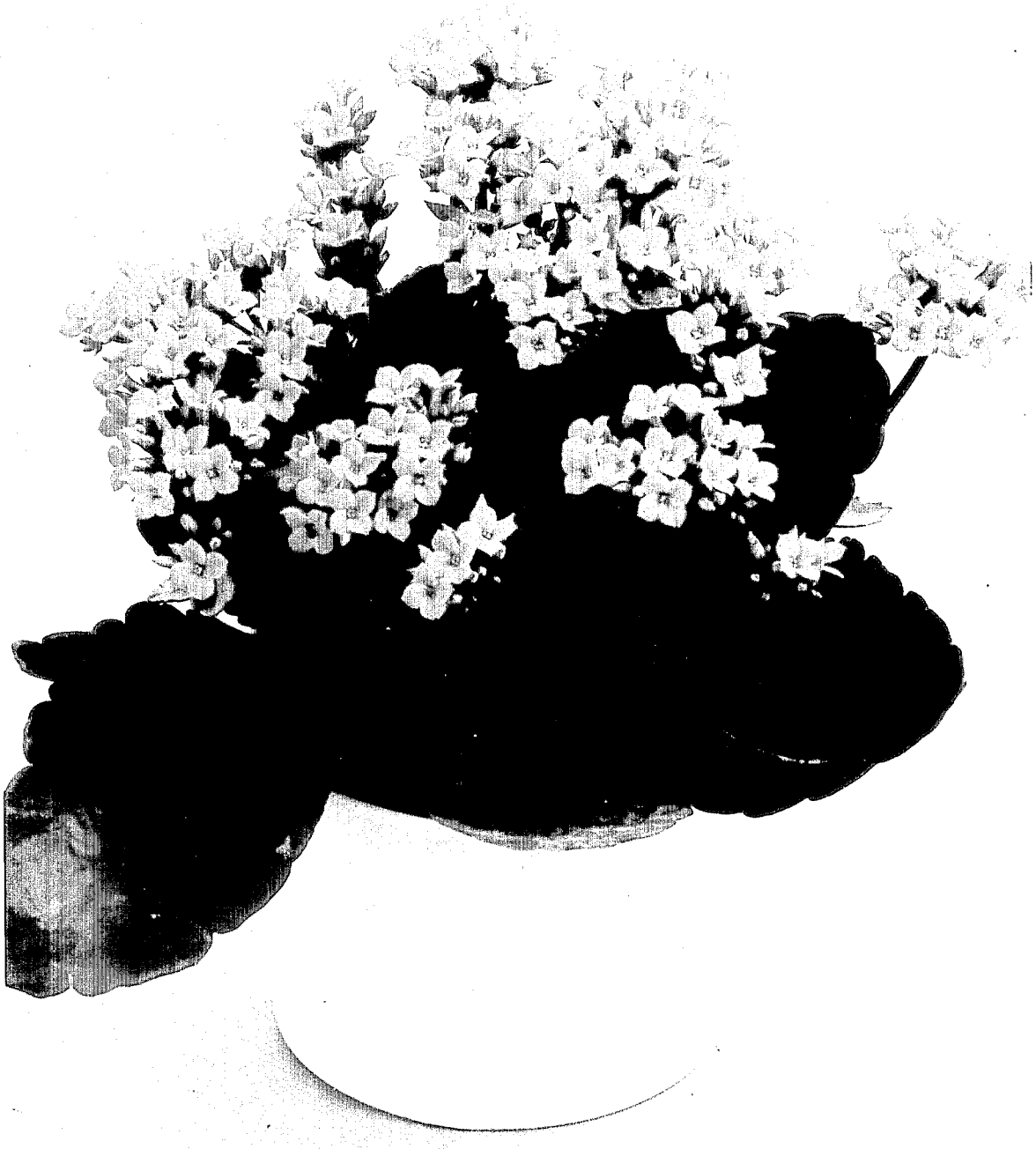

* * * * *